United States Patent [19]

Hertl et al.

[11] 4,052,504
[45] Oct. 4, 1977

[54] ASSAY FOR THYROXINE BINDING GLOBULIN

[75] Inventors: William Hertl, Corning; Gerald Odstrchel, Horseheads, both of N.Y.

[73] Assignee: Corning Glass Works, Corning, N.Y.

[21] Appl. No.: 701,191

[22] Filed: June 30, 1976

[51] Int. Cl.$^2$ .................. G01N 33/00; G01N 33/16
[52] U.S. Cl. ........................... 424/1; 23/230 B; 424/12
[58] Field of Search ............... 424/1, 1.5, 12; 23/230 B, 230.6

[56] References Cited

U.S. PATENT DOCUMENTS

| 3,799,740 | 3/1974 | Mincey | 424/1 |
| 3,929,981 | 12/1975 | Murty et al. | 424/1 |
| 3,960,492 | 6/1976 | DiGiulio | 23/230 B |

Primary Examiner—Benjamin R. Padgett
Assistant Examiner—Christine M. Nucker
Attorney, Agent, or Firm—James A. Giblin; Clinton S. Janes, Jr.; Clarence R. Patty, Jr.

[57] ABSTRACT

Method of determining the concentration of thyroxine binding globulin (TBG) in a fluid sample. The method comprises the steps of adding to the sample an excess amount of thyroxine ($T_4$) and then analyzing the sample for $T_4$ via immunoassay technique in the presence and absence of a blocking agent to establish a binding differential. The differential is then correlated with a standard curve which relates known TBG concentrations to binding differentials obtained in a similar manner.

6 Claims, No Drawings

4,052,504

ASSAY FOR THYROXINE BINDING GLOBULIN

RELATED APPLICATION

Patent application Ser. No. 701,192, entitled "Assay for Free Thyriod Hormones", filed of even date in the names of W. Hertl and G. Odstrchel and assigned to the same assignee as this application.

BACKGROUND OF THE INVENTION

This disclosure relates generally to the field of immunoassays and specifically with immunoassays used to determine concentrations of triiodothyronine ($T_3$), thyroxine ($T_4$) and thyroxine binding globulin (TBG) in a fluid sample such as blood serum.

In a radioimmunoassay (RIA) for $T_3$ or $T_4$, it is known that the use of blocking agents (sometimes referred to as deblocking agents) improves the assay by either allowing the competitive binding to go faster or by changing the equilibrium point. In general, the function of the blocking agent is to displace the $T_3$ or $T_4$ from serum proteins, primarily TBG. Substances that act as blocking agents incude 8-anilino-1-naphthalenesulfonic acid (ANS), merthiolate (thimerosal), dilantin, and many other substances. Such blocking agents and their use in a RIA of $T_3$ or $T_4$ are described, for example, in U.S. Pat. No. 3,911,096 to I. J. Chopra, the teachings of which are incorporated herein by reference.

Because one of the essential steps in most RIA's involves the separation of labeled immunochemically complexed products from radio labelled substances which are not so complexed, attention has been drawn recently to the use of solid phase techniques in RIA. Solid phase RIA (SPRIA) involves the use of an insoluble carrier to which antibodies or antigenic substances can be attached in an active form. Since the solid phase is insoluble, the RIA separation step is facilitated. Examples of the various carrier materials which can be used in SPRIA can be founrd in U.S. Pat. No. 3,555,143 to Axen et al. (organic carriers) and U.S. Pat. No. 3,652,761 to Weetall (inorganic carriers).

In preliminary investigations of the reaction kinetics of a typical SPRIA using an immobilized antibody (IMA) to thyroxine, we found that the complexation rate was definable as:

$$\text{Rate} = [FT_4][IMA],$$

where $[FT_4]$ represents the free $T_4$ concentration. By combining this observation with a further observation that blocking agents in $T_4$ assays serve primarily to displace $T_4$ from TBG (an $\alpha$-globulin), we were led to the discovery that TBG concentrations could be determined by a novel method, the details of which are described herein.

SUMMARY OF THE INVENTION

Our method of determining the concentration of TBG in a fluid sample comprises adding to the sample an excess amount of $T_4$ and then analyzing the sample via immunoassay technique in both the presence and absence of a blocking agent to establish a binding differential; and then correlating that differential with a standard curve relating known TBG concentrations to binding differentials. In a preferred embodiment the immunoassay is a solid phase radioimmunoassay using anti-$T_4$ antibodies attached to a water-insoluble carrier. Preferably the excess amount of $T_4$ added to the sample comprises at least about 200 ng of $T_4$ per ml sample and the binding differential is represented by the difference between the percent of the thyroid hormone bound with and without the blocking agent divided by the percent of $T_4$ bound with the blocking agent. As especially preferred carrier comprises silanized glass particles and preferred blocking agents include ANS, or a salt thereof, and merthiolate.

SPECIFIC EMBODIMENTS

Very important to our method of measuring TBG concentrations is the determination of % binding of $T_4$ to anti-$T_4$ antibodies in the presence and absence of a blocking agent. Although it is thought that the technique disclosed herein is equally applicable to a variety of immunoassay methods (e.g. fluoroimmunoassays, enzyme-immunoassays, etc.), radioimmunoassays are especially preferred because of their current usage and sensitivity. SPRIA's are especially preferred because they permit rapid separation of bound constituents from unbound constituents.

As indicated above, our experimentation in the field of SPRIA for $T_4$ showed that $$\text{Rate} = [FT_4][IMA]$$

where $FT_4$ represents free (unbound) $T_4$ and IMA represents the amount of immobilized anti-$T_4$ antiserum (e.g. anti-$T_4$ attached to silanized glass particles). The IMA concentration is fixed in a given SPRIA but the concentration of $FT_4$ depends on both the total $T_4$ concentration and the concentration of the binding protein, in this case, the TBG. The extent of binding is determined by the association constant. Since in samples of practical interest (e.g. blood serum), the total $T_4$ will vary as well as the TBG which is to be measured, we found that it was very important to take into account the quantity of $T_4$ present in an assay for TBG.

We have found that by adding a relatively large amount of $T_4$ (excess $T_4$) to a fluid sample containing both $T_4$ and TBG, TBG concentrations could be determined in a manner similar in principal to that disclosed in the related application cited above. The cited application is concerned with determining free thyroid hormone (e.g. $T_4$) concentrations by assaying for total thyroid hormone in the presence and absence of a blocking agent to establish a binding differential which, in turn, is related to free thyroid hormone concentration.

The actual amount of $T_4$ added to the sample containing the unknown TBG should be enough to substantially eliminate sample to sample variation in $T_4$ concentration. Although the "normal" total $T_4$ concentration may range from about 80 to 120 ng/ml of human serum, it is known that in some cases (abnormal) the $T_4$ concentration may be as high (or possibly higher) than about 200 ng/ml. Accordingly, we have found that the effect of variation of $T_4$ levels can be greatly minimized by simply adding an excess amount of $T_4$ to the sample prior to the immunoassays so that the $T_4$ variation from sample to sample is essentially masked, thereby making the differential technique highly sensitive to only the TBG concentration.

As a practical matter, we found that by adding at least about 200 ng of $T_4$ to a ml of the sample, the variation in overall reaction rates is independent of the $T_4$ initially present in the sample. Indeed, the addition of 400 ng/ml of $T_4$ to the sample resulted in essentially identical results (standard curves). Accordingly, the expression excess amount of $T_4$, as used herein, refers to at least about 200 ng/ml of $T_4$ to each ml of an unknown fluid sample.

Our overall technique is illustrated below where we describe the preparation of a standard curve and the use of that curve to determine TBG values having known TBG values. In the experiments described below, the immunoassay test system used was a commercially available SPRIA $T_4$ ket (IMMOPHASE ©, $T_4$, Corning Glass Works). The kit was used as directed, except for the parallel experiments where the blocking agent was eliminated.

PREPARATION OF STANDARD CURVE

Samples were made up containing known amounts of TGB in 3.5% bovine serum albumin (BSA). In one set of experiments an excess amount of $T_4$, at the amount of 200 ng/ml, was added, to each sample. In a parallel set of experiments, an amount of $T_4$ equal to 400 ng/ml was added. Then, SPIRA's were performed on each set of samples in the presence of a common blocking agent (merthiolate), as required by the kit, and in the absence of the blocking agent. The percent of $T_4$ bound in each case was determined by standard means (counting $^{125}I$-$T_4$) and a binding differential $\Delta B$ was established by simply substracting the % $T_4$ bound without the blocking agent from the % $T_4$ bound with the blocking agent ($B_{block}$). This differential was then normalized by dividing by $B_{block}$ and the result multiplied by 100 to give a whole number represented as $\Delta B/B_{block} \times 100$. The respective differentials were then plotted against the known TBG concentrations upon which the differentials were determined. The results for both sets of experiments are summarized in the Table below.

TABLE I

| (Standard Curve Data) | | |
|---|---|---|
| | - Differential - $\Delta B/B_{block} \times 100$ | |
| Known TBG (µg/ml) | Excess T = 200 ng/ml | Excess T = 400 ng/ml |
| 6 | 12 | 14 |
| 12.5 | 19 | 18 |
| 25 | 27 | 26 |
| 50 | 45 | 47 |
| 100 | 62 | 68 |

Another set of samples was made up with known TBG concentrations and the respective differential rates were measured. The differential rates ($B/B_{block} \times 100$) were then used to determined TBG concentrations by reading the values from the standard curve. The following values for TBG were obtained:

TABLE II

| | TBG conc. (µg/ml) | |
|---|---|
| Known Concentrations | Via Differential Analysis from $\Delta B/B_{block} \times 100$ |
| 100 | 96 |
| 50 | 54 |
| 25 | 33 |
| 12.5 | 12 |
| 6 | 4.8 |

The agreement can be considered clinically satisfactory. The "normal" range of TBG values in human blood serum is thought to be about 10 to 20 ug/ml.

It is thought that, given this disclosure, numerous variations within the spirit of this invention will become apparent to those skilled in this field. Accordingly, it is intended that the scope of this invention should be limited only by the following claims.

We claim:

1. A method of determining the concentration of thyroxine binding globulin in a sample, the method comprising the steps of
   1. adding to the sample an excess amount of thyroxine;
   2. analyzing the sample for thyroxine via separate immunoassays, one immunoassay being in the presence of a blocking agent and the other immunoassay being in the absence of a blocking agent to thereby establish a binding differential; and
   3. then correlating that differential with a standard curve which relates known thyroxine binding globulin concentrations with binding differentials.

2. The method of claim 1 wherein the excess thyroxine comprises at least about 200 ng of thyroxine per ml of sample.

3. The method of claim 1 wherein the immunoassay technique for analyzing for thyroxine is a radioimmunoassay.

4. The method of claim 1 wherein the radioimmunoassay technique is a solid phase radioimmunoassay technique using silanized glass particles as carriers for the anti-thyroxine antibodies.

5. The method of claim 1 wherein the binding differential is represented by the difference between the amount of thyroxine bound with and without the use of a blocking agent divided by the amount of thyroxine bound with a blocking agent.

6. The method of claim 1 wherein the blocking agent is thimerosal or 8-anilino-1-naphthalenesulfonic acid.

* * * * *

UNITED STATES PATENT AND TRADEMARK OFFICE
CERTIFICATE OF CORRECTION

PATENT NO.    : 4,052,504
DATED         : October 4, 1977
INVENTOR(S)   : William Hertl and Gerald Odstrchel It is certified that error appears in the above-identified patent and that said Letters Patent are hereby corrected as shown below:

Column 1, line 38, "founrd" should be -- found --.

Column 1, line 68, after "ml" insert -- of --.

Column 3, line 9, "ket (IMMOPHASE C ," should be -- kit (IMMOPHASE®, --.

Column 3, line 17, "TGB" should be -- TBG --.

Column 4, line 15, "ug/ml." should be -- µg/ml. --.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks